(12) United States Patent  (10) Patent No.: US 8,457,740 B2
Osche  (45) Date of Patent: Jun. 4, 2013

(54) DEVICE FOR DETERMINING AN AFTERCARE APPOINTMENT FOR THE SUPPLY OF AN IMPLANTABLE MEDICAL DEVICE

(75) Inventor: Thomas Osche, Berlin (DE)

(73) Assignee: BIOTRONIK CRM Patent AG (CH)

( * ) Notice: Subject to any disclaimer, the term of this patent is extended or adjusted under 35 U.S.C. 154(b) by 948 days.

(21) Appl. No.: 12/251,493

(22) Filed: Oct. 15, 2008

(65) Prior Publication Data

US 2009/0112290 A1  Apr. 30, 2009

(30) Foreign Application Priority Data

Oct. 30, 2007 (DE) .......................... 10 2007 051 756

(51) Int. Cl.
*A61N 1/00* (2006.01)
*A61B 5/00* (2006.01)
*A61B 5/05* (2006.01)

(52) U.S. Cl.
USPC ...... 607/27; 607/6; 607/30; 607/31; 600/300; 600/547

(58) Field of Classification Search
USPC .................. 607/6, 27, 30–31; 600/300, 547
See application file for complete search history.

(56) References Cited

U.S. PATENT DOCUMENTS

| 2001/0025137 | A1 | 9/2001 | Webb et al. |
| 2003/0028082 | A1 | 2/2003 | Thompson |
| 2003/0144711 | A1 | 7/2003 | Pless |
| 2006/0265020 | A1* | 11/2006 | Fischell et al. ................. 607/30 |
| 2007/0060797 | A1* | 3/2007 | Ball et al. ..................... 600/300 |

FOREIGN PATENT DOCUMENTS

WO  WO 2007/027570 A  3/2007

* cited by examiner

*Primary Examiner* — Nicole F Lavert
(74) *Attorney, Agent, or Firm* — Craig A. Fieschko, Esq.; DeWitt Ross & Steven S.C.

(57) ABSTRACT

The invention relates to a service unit (30) having an interface (54) for receiving data from a personal medical device, an analysis unit (52) connected to the interface (54) for analyzing data received from the personal medical device (10), and an aftercare appointment determination unit (54) for determining a particular next aftercare appointment at least on the basis of data received from a particular personal medical device (10).

21 Claims, 2 Drawing Sheets

Figure 1:
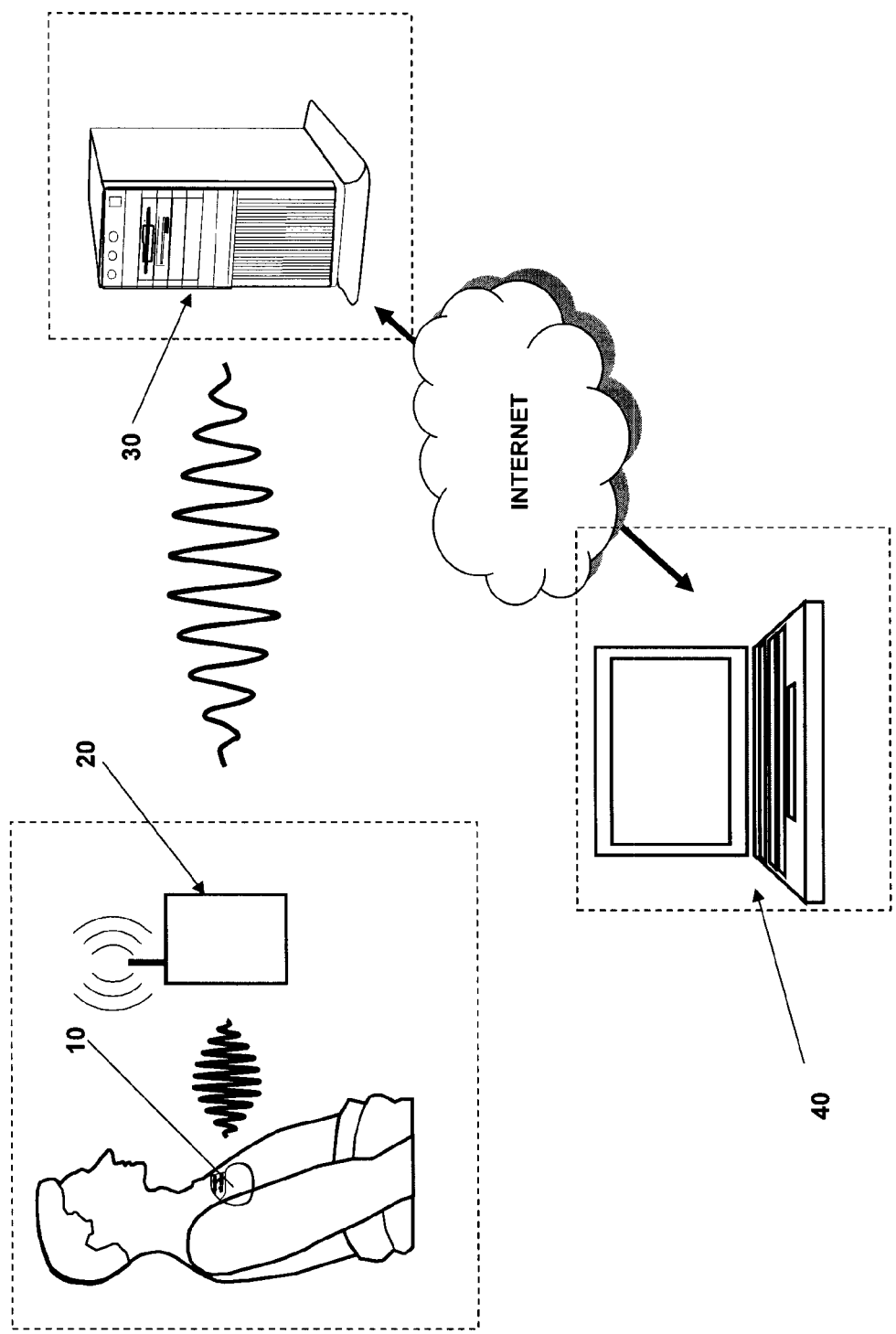

DEVICE FOR DETERMINING AN AFTERCARE APPOINTMENT FOR THE SUPPLY OF AN IMPLANTABLE MEDICAL DEVICE

FIELD OF THE INVENTION

The invention relates to a device for determining an aftercare appointment for a medical implantable device, in particular for an electrostimulator such as a cardiac pacemaker, a cardioverter/defibrillator, or the like.

BACKGROUND OF THE INVENTION

Implantable medical devices, such as cardiac pacemakers, are known wherein data detected by the cardiac pacemaker or generated by the cardiac pacemaker is transmitted to a central service unit. The data transmission required for this purpose is performed wirelessly via a comparatively relatively short range from the implant to an external device, for example, which is located in the range of the implant for the purposes of the data transmission. The external device functions as a quasi-relay station and is implemented for the purpose of transmitting the data sent from the implant further to the central service unit. The data may be analyzed in a central service unit and be available centrally to a physician. This can to some extent allow remote diagnoses, which may partially replace personal visits of the physician to the patient or vice versa. In addition, a system of this type allows the physician to be able to recognize possibly critical health statuses early, to which he may then react rapidly, possibly even before the patient himself notices a critical health status.

In addition, various systems are known from the prior art which support the physician in the aftercare of a patient. Examples are found in U.S. Pat. No. 6,648,823, US 2003/028082, and US 2005/0065555.

SUMMARY OF THE INVENTION

An object of the present invention is to find an improved device which supports an aftercare of a patient. In particular, a device is desired which supports the physician in finding a suitable aftercare appointment.

The object is achieved according to the invention by a service unit which has a first interface for receiving data on the part of a personal medical device, in particular an implantable medical device such as a cardiac pacemaker or cardioverter/defibrillator. Furthermore, the service unit has an analysis unit for analyzing data received on the part of the personal medical device. The analysis unit is connected to the first interface. Finally, the service unit has an aftercare appointment determination unit, which is connected to the analysis unit and is implemented to determine a particular next aftercare appointment at least on the basis of the data received on the part of the personal medical device.

The invention is based on the finding that the data received on the part of the personal medical device contain precisely the information which is relevant for determining an aftercare appointment. These data typically also contain, in addition to device-specific data, which provides information about the technical status of the particular personal medical device, physiological data, which were detected on the part of the personal medical device and which permit a conclusion about the health status of a particular patient. For example, if the data for a particular personal medical device indicate that the personal medical device is to be operationally ready for a long time and simultaneously the physiological data indicate a good health status of the patient, an aftercare appointment may be selected in the relatively far future. Vice versa, if the data for a particular personal medical device make it obvious, for example, that the personal medical device itself requires earlier attention, for example, in the case of the occurrence of operational errors or imminent exhaustion of the battery capacity or if the physiological data indicate that the health status of the patient is not as good as desired, an earlier aftercare appointment may be indicated.

According to the invention, a particular aftercare appointment is thus determined automatically by the aftercare appointment determination unit individually and as a function of current data originating from the particular personal medical device. It is thus not established in the meaning of a regularly repeating interval by the aftercare appointment determination unit. Rather, by determining a particular next aftercare appointment, the aftercare appointment determination unit solely determines the interval from the particular instant up to this next aftercare appointment.

According to a preferred version of the invention, the service unit has a memory in which at least one preceding aftercare appointment is to be stored. The service unit may also have an access to such a memory. The aftercare appointment determination unit is implemented, for the determination of a next aftercare appointment, to take the stored datum of a preceding aftercare appointment into consideration in addition to the data received on the part of the personal medical device.

The data used by the aftercare appointment determination unit for determining a particular next aftercare appointment thus comprise, according to a preferred version of the invention, firstly at least the data of the aftercare appointment which has most recently already occurred, as well as data received on the part of the personal medical device, namely physiological data acquired by the personal medical device and operational data for the personal medical device.

According to a further preferred version of the invention, the service unit has a second interface as an interface for user inputs, also referred to as a user input unit hereafter. The aftercare appointment determination unit is implemented to accept user inputs and also process them for determining a next aftercare appointment. This allows, inter alia, a particular physician to be able to influence the determination of a next aftercare appointment and be able to easily compare the next aftercare appointment to his personal calendar, for example. The physician also thus has the capability of making a next aftercare appointment dependent on further circumstances which are not accessible to the aftercare appointment determination unit. For example, when determining a next aftercare appointment, the physician may also consider the circumstance that a particular patient, desires especially intensive medical care.

In this context, it is especially preferable if the service unit is implemented together with the aftercare appointment determination unit to display a particular aftercare appointment determined by the aftercare appointment determination unit and to accept a user input in reaction thereto, using which a user either accepts an aftercare appointment which has been displayed or rejects it and replaces it with another aftercare appointment established by the user. Displaying data for the next aftercare appointment means that the service unit generates data which permit a display of a next aftercare appointment on a suitable display device. In this meaning, displaying may also include the transmission of a message, such as an SMS message, or possibly also an audible message, to a particular user.

In regard to the preferred version of the invention, which permits the physician to replace an aftercare appointment determined automatically by the aftercare appointment determination unit with a self-selected aftercare appointment, it is to be noted that also in this case the preceding automatic determination of a next aftercare appointment is of great utility for the physician. This is because the next aftercare appointment automatically determined by the aftercare appointment determination unit already contains an indication to the physician of how urgent or less urgent a personal visit is for a particular patient (or vice versa). For example, if the physician establishes that he would himself have suggested a significantly deviating aftercare appointment, he may review the data used by the aftercare appointment determination unit to convince himself once again personally of the urgency recognized on the part of the aftercare appointment determination unit, for example.

In addition, the aftercare appointment determination unit may be implemented so that it analyzes user-determined aftercare appointments in relation to the particular automatically determined aftercare appointment and ascertains typical deviations between the user-determined aftercare appointment and automatically determined aftercare appointment and stores these typical deviations. For example, a typical deviation may be that a user-determined aftercare appointment selected by a physician in each case in response to an automatically determined aftercare appointment regularly lies before the automatically determined aftercare appointment, because the patient desires especially intensive medical care, for example. A typical deviation of this type may be automatically ascertained and stored by the aftercare appointment determination unit. The aftercare appointment determination unit is then preferably implemented to also consider typical deviations ascertained in this manner for the determination of an automatically determined aftercare appointment. The aftercare appointment determination unit "learns" in this manner, for example, to regularly determine rather earlier aftercare appointments in connection with specific personal medical devices (and thus in connection with specific patients).

If a particular next aftercare appointment is established—either automatically determined or possibly altered by the user—the service unit provides this final aftercare appointment to a user, preferably in a printout. The service unit may include an appropriate third interface for this purpose.

It is to be noted that the suggested service unit having the corresponding aftercare appointment determination unit fundamentally only requires unidirectional data communication from the personal medical device to the service unit. The service unit according to the invention may also be used in a system in which a bidirectional data connection is possible between the service unit and the personal medical device.

Figure 2:
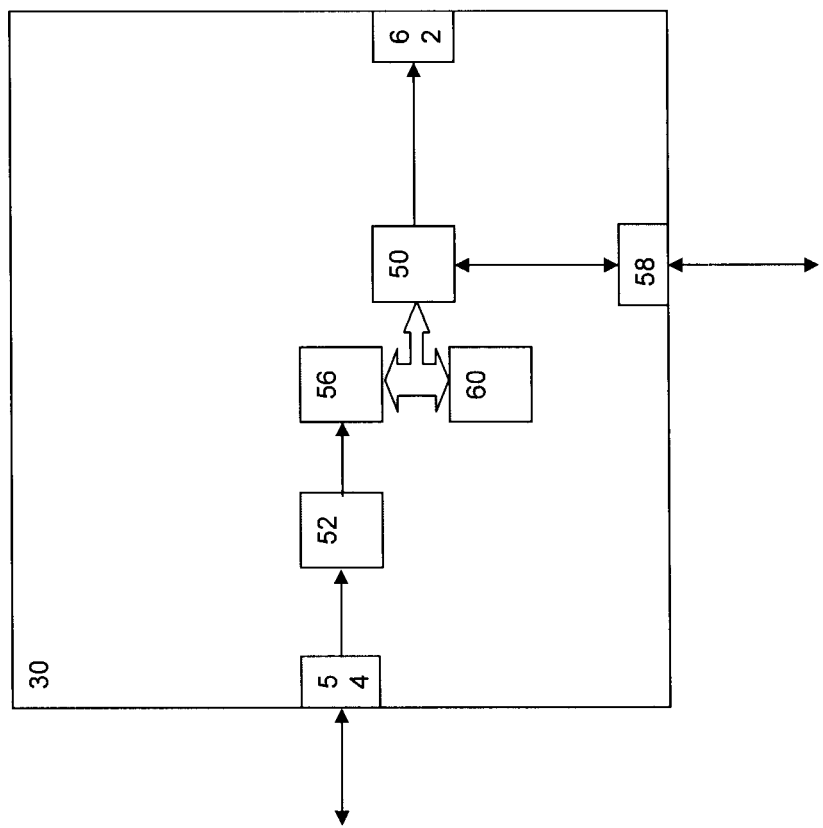

The invention will be explained in greater detail on the basis of an exemplary version of the invention with reference to the figures. In the figures:

FIG. 1: shows an overview of a medical therapy system having a personal medical device in the form of a cardiac pacemaker and a service unit in the form of a central server;

FIG. 2: shows a schematic block diagram of a service unit according to the invention.

FIG. 1 shows a medical therapy system, which primarily includes a personal medical device 10 in the form of an implanted cardiac pacemaker and/or implanted cardioverter/defibrillator. The personal medical device 10 may communicate at least unidirectionally with an external device 20 to transmit data from the personal medical device to the external device 20 in this manner. In a manner known per se, the personal medical device 10 has sensors for acquiring physiological data, for example, for acquiring natural heart contractions and data derived therefrom, such as data in regard to a natural heart rate or in regard to the presence of a fibrillation or similar state. In addition, the personal medical device is also implemented to acquire operational data about its own operational state, such as the charge state of its batteries, and to transmit this data at regular or irregular intervals to the external device 20.

The external device 20 is used as a relay station and is connected to a central service unit 30. The data connection between the external device 20 and the central service unit 30 may be wired or wireless. For example, a connection via Virtual Private Network (VPN) is possible.

The central service unit is additionally connected via the Internet, for example, to a terminal 40, such as a personal computer of a user (physician). It is possible via the terminal 40 to display data received on the part of the central service unit 30 or to accept user inputs and to transmit corresponding data to the central service unit 30. The special feature of the system shown is that the service unit 30 is implemented to determine an aftercare appointment (follow-up appointment) automatically, at which physician and patient are to meet for an aftercare examination.

For this purpose, the service unit 30 has an aftercare appointment determination unit 50, which is implemented to determine a particular next aftercare appointment on the basis of data which the service unit 30 has received on the part of a particular personal medical device 10. To receive data of this type, the service unit 30 has a data interface 54 as a first interface and an analysis unit 52 connected thereto. The analysis unit 52 is implemented to analyze the data received on the part of the personal medical device 10 and to store it either in the analyzed state or also as raw data in a memory 56. The aftercare appointment determination unit 50 may also access this memory 56.

The aftercare appointment determination unit 50 determines a next aftercare appointment on the basis of the data stored in the memory 56. The data stored in the memory 56 are preferably:

measured data of electrical and nonelectrical external sensors of the personal medical device (implant) 10;

data on the system integrity of electrical and nonelectrical external sensors and electrical and nonelectrical actuators of implant 10;

data on the system integrity of the implant;

data which have been ascertained in the implant 10, or outside in the scope of a model calculation, about the physiological status of a patient;

data which have been ascertained in the implant 10, or outside in the scope of a model calculation, about the technical state of the implant 10; and/or data which have been ascertained in the implant 10 in the scope of a model calculation of the technical state of the electrical and nonelectrical actuators and sensors of implant 10.

The data ascertained in the scope of a model calculation are preferably obtained by the analysis unit 52 from the raw data received on the part of the personal medical device. Alternatively, data may also be ascertained in the context of a model calculation already in the personal medical device 10.

The personal medical device (implant) 10 is preferably implemented to transmit the corresponding data daily to the central service unit 30. For this purpose, only a unidirectional data communication is fundamentally required between the personal medical device 10 and the central service center 30. In the case of a possible bidirectional data connection between the implant 10 and the central service unit 30, the service unit 30 may also be implemented to request the corresponding data on the part of the personal medical device 10 daily.

The aftercare appointment determination unit 50 is additionally connected to a second memory 58, which is used for storing preceding aftercare appointments. The two memories 56 and 58 may be the same physical memory and may thus represent different memory areas of the same physical memory.

The aftercare appointment determination unit 50 automatically ascertains at least one next aftercare appointment on the basis of the data stored in the memories 56 and 58 in the manner as explained in the introduction to the description.

The data representing the next aftercare appointment automatically determined in this manner are provided via a further data interface 60 so that they may be viewed on a display by a physician, for example. In the exemplary embodiment, the interface 60 is preferably an interface to the Internet which allows a particular automatically determined aftercare appointment to be shown on the display of the personal terminal 40, for example.

The aftercare appointment determination unit is simultaneously implemented so that it permits a user input in reaction to the display of an automatically ascertained aftercare appointment in such a manner that either the automatically determined aftercare appointment is confirmed on the part of the user (i.e., the physician), or the user rejects the automatically determined aftercare appointment. The aftercare appointment determination unit 50 is implemented to allow the manual input of a next aftercare appointment via the keyboard of the personal terminal 40, for example, in reaction to the latter case.

If a user confirms the automatically determined aftercare appointment, this automatically determined aftercare appointment is established as the next aftercare appointment. If the user rejects the automatically determined aftercare appointment and replaces it with a user-determined aftercare appointment to be input manually, the user-determined aftercare appointment is established as the next aftercare appointment.

The aftercare appointment determination unit 50 stores the next aftercare appointment established in this manner in the memory 58 and additionally ensures that the established next aftercare appointment is logged by a printout. For this purpose, the aftercare appointment determination unit 50 is connected to a corresponding printer interface 62 of the service unit 30.

In this context, the aftercare appointment determination unit 50 is also implemented, in addition to a particular next aftercare appointment, to concurrently print out contact data and possibly further data for a particular patient applying to the aftercare appointment. For this purpose, the aftercare appointment determination unit 50 is connected to a patient data databank.

A special feature of the aftercare appointment determination unit 50 is that it is implemented to consider user inputs for the determination of a particular next aftercare appointment. In the simplest case, these are the user inputs using which a user rejects an automatically prepared aftercare appointment and instead inputs a user-determined aftercare appointment. The aftercare appointment determination unit 50 is implemented to analyze these aftercare appointments input by the user per se and in relation to particular automatically determined aftercare appointments in such a manner that the aftercare appointment determination unit 50 recognizes typical patterns automatically. A pattern of this type may comprise, for example, the user-determined aftercare appointment predefined by a physician regularly being before the automatically determined aftercare appointment. For this case, the aftercare appointment determination unit 50 is implemented to consider the pattern thus recognized in the automatic determination of a next aftercare appointment and to determine an earlier aftercare appointment than it would otherwise indicate on the basis of the remaining data used for determining the particular next aftercare appointment.

In this manner, the aftercare appointment determination unit 50 is capable of quasi-learning the preferences of a physician.

The latter is made easier in particular if the aftercare appointment determination unit is implemented to regularly determine not only a single next aftercare appointment, but rather a plurality of alternatives for a next aftercare appointment, for example, among which the physician may then select the particular aftercare appointment appearing most suitable to him. If regular patterns result from this selection—for example, regular selection of the particular earliest or latest of the offered aftercare appointments—this may be taken into consideration still more easily in the determination of a particular next aftercare appointment or in the determination of a plurality of sequential aftercare appointments.

What is claimed is:

1. A service unit (30) having:
    a. an interface (54) for receiving data from a personal medical device (10),
    b. an analysis unit (52) configured to analyze data received from the personal medical device (10), the analysis unit being connected to the interface (54),
    c. an aftercare appointment determination unit (50) connected at least indirectly to the analysis unit (52) and/or the interface (54), wherein the aftercare appointment determination unit (50) is configured to schedule the time of a next aftercare appointment at least partially on the basis of data received from the personal medical device (10).

2. The service unit (30) of claim 1 wherein the data received from the personal medical device (10) include one or more of:
    a. data reflecting the physiological status of a patient bearing the personal medical device (10), and
    b. data representing the operational integrity of the personal medical device (10).

3. The service unit (30) of claim 1 wherein:
    a. the service unit (30) is in communication with a memory (58) containing at least one preceding aftercare appointment, and
    b. the aftercare appointment determination unit (50) is configured to also schedule the time of the next aftercare appointment at least partially in dependence on the date of the preceding aftercare appointment.

4. The service unit (30) of claim 1 wherein:
    a. the service unit (30) is in communication with a user input unit (40), and
    b. the aftercare appointment determination unit (50) is configured to also schedule the time of the next aftercare appointment at least partially in dependence on user inputs received from the user input unit (40).

5. The service unit (30) of claim 4 wherein the service unit (30) is configured to, after scheduling the time of a next aftercare appointment by the aftercare appointment determination unit (50):
    a. display the next aftercare appointment to a user, and
    b. accept a user input indicative of acceptance or rejection of the displayed aftercare appointment.

6. The service unit (30) of claim 5 wherein the service unit (30) is configured, upon acceptance of a user input indicative of rejection of the displayed aftercare appointment, to collect and store a user input of a user-determined aftercare appointment.

7. The service unit (30) of claim 6 wherein the aftercare appointment determination unit (50) is configured to:
   a. analyze deviations between stored user-determined aftercare appointments in relation to aftercare appointments scheduled by the aftercare appointment determination unit (50), and
   b. schedule the time of the next aftercare appointment at least partially in dependence on the deviations.

8. The service unit (30) of claim 1 wherein:
   a. the aftercare appointment determination unit (50) is configured to automatically schedule the times of several alternative next aftercare appointments, and
   b. the service unit (30) is configured to:
      (1) display the several alternative aftercare appointments, and
      (2) accept a user input indicative of:
         i. acceptance of one of the displayed aftercare appointments, or
         ii. rejection of all of the displayed aftercare appointments,
      at a user input unit (40).

9. The service unit (30) of claim 1 wherein the personal medical device (10) is an implantable electrostimulation device.

10. The service unit (30) of claim 9 wherein the implantable electrostimulation device is a cardiac pacemaker and/or a cardioverter/defibrillator.

11. A method of determining an aftercare appointment for a patient bearing an implantable electrostimulation device, the method including the steps of:
   a. receiving data from an implantable electrostimulation device (10) at an interface (54),
   b. define the time of a next aftercare appointment within an aftercare appointment determination unit (50), the time of the next aftercare appointment being defined at least partially in dependence on data received from the implantable electrostimulation device (10),
   c. displaying the next aftercare appointment to the patient, and
   d. accepting at a user input unit (40) patient input indicative of the patient's acceptance or rejection of the displayed next aftercare appointment.

12. The method of claim 11 wherein the data received from the implantable electrostimulation device (10) include one or more of:
   a. data reflecting the physiological status of a patient bearing the implantable electrostimulation device (10), and
   b. data representing the operational integrity of the implantable electrostimulation device (10).

13. The method of claim 11 wherein:
   a. the service unit (30) is in communication with a memory (58) containing at least one preceding aftercare appointment, and
   b. the aftercare appointment determination unit (50) also defines the time of the next aftercare appointment at least partially in dependence on the date of the preceding aftercare appointment.

14. The method of claim 11 further including the step of collecting and storing a user input of a user-determined aftercare appointment if the patient input is indicative of the patient's rejection of the displayed next aftercare appointment.

15. The method of claim 14 wherein the aftercare appointment determination unit (50):
   a. analyzes deviations between stored user-determined aftercare appointments in relation to next aftercare appointments defined by the after-care appointment determination unit (50), and
   b. defines the next aftercare appointment at least partially in dependence on the deviations.

16. The method of claim 11 wherein:
   a. the aftercare appointment determination unit (50) automatically defines several alternative next aftercare appointments, and
   b. the service unit (30):
      (1) displays the several alternative next aftercare appointments, and
      (2) accepts a user input indicative of:
         i. acceptance of one of the displayed next aftercare appointments, or
         ii. rejection of all of the displayed next aftercare appointments,
      at a user input unit (40).

17. The method of claim 11 wherein the data from the implantable electrostimulation device (10) is wirelessly transmitted from the implantable electrostimulation device (10).

18. The method of claim 11 wherein the next aftercare appointment is also determined at least partially in dependence on data received from the patient's physician, the data being indicative of the physician's availability.

19. The method of claim 11 further including the steps of:
   a. displaying the next aftercare appointment to the patient's physician, and
   b. accepting physician input indicative of the physician's acceptance or rejection of the displayed next aftercare appointment.

20. The method of claim 11 further including the step of delivering to the patient a printed message confirming the next aftercare appointment.

21. A method of determining an aftercare appointment for a patient bearing an implantable electrostimulation device, the method including the steps of:
   a. receiving data wirelessly transmitted from an implantable electrostimulation device (10) at a service unit (30),
   b. determining the next aftercare appointment time within the service unit (30) at least partially in dependence on:
      (1) data received from the implantable electrostimulation device (10), the data including one or more of:
         i. data reflecting the physiological status of a patient bearing the implantable electrostimulation device (10), and
         ii. data representing the operational integrity of the implantable electrostimulation device (10);
      (2) data received from the patient, the data being indicative of the patient's desired scheduling of the next aftercare appointment; and
      (3) data received from the patient's physician, the data being indicative of the physician's availability;
   c. providing the determined next aftercare appointment to the patient.

* * * * *